US011183380B2

(12) United States Patent
Riepe et al.

(10) Patent No.: US 11,183,380 B2
(45) Date of Patent: Nov. 23, 2021

(54) GERMICIDAL AMALGAM LAMP WITH TEMPERATURE SENSOR FOR OPTIMIZED OPERATION

(71) Applicant: Xylem Europe GmbH, Schaffhausen (CH)

(72) Inventors: Dirk Riepe, Herford (DE); Uwe Kanigowski, Velbert (DE); Jan Boris Loesenbeck, Bielefeld (DE); Sven Kaemmerer, Bad Salzuflen (DE)

(73) Assignee: Xylem Europe GbmH

(*) Notice: Subject to any disclaimer, the term of this patent is extended or adjusted under 35 U.S.C. 154(b) by 0 days.

(21) Appl. No.: 16/964,664

(22) PCT Filed: Jan. 24, 2019

(86) PCT No.: PCT/EP2019/051791
§ 371 (c)(1),
(2) Date: Jul. 24, 2020

(87) PCT Pub. No.: WO2019/145445
PCT Pub. Date: Aug. 1, 2019

(65) Prior Publication Data
US 2021/0057205 A1 Feb. 25, 2021

(30) Foreign Application Priority Data
Jan. 24, 2018 (EP) .................................... 18153198

(51) Int. Cl.
*H01J 61/56* (2006.01)
*A61L 2/10* (2006.01)
(Continued)

(52) U.S. Cl.
CPC ................ *H01J 61/56* (2013.01); *A61L 2/10* (2013.01); *C02F 1/325* (2013.01); *H01J 7/44* (2013.01);
(Continued)

(58) Field of Classification Search
CPC ........... H01J 61/06–28; H01J 61/52–56; H01J 61/82–827; H01J 7/02–22; C02F 1/32–325; H05B 41/2851–2858
See application file for complete search history.

(56) References Cited

U.S. PATENT DOCUMENTS 3,859,555 A * 1/1975 Latassa .................. H01J 61/72
313/490
4,302,677 A 11/1981 Albertsson et al.
(Continued)

FOREIGN PATENT DOCUMENTS

CN          1489176 A  *  4/2004
CN       210065244 U  *  2/2020
(Continued)

OTHER PUBLICATIONS

International Search Report and Written Opinion for International Application No. PCT/EP2019/051791, dated Apr. 30, 2019, 12 pages.
(Continued)

*Primary Examiner* — Mariceli Santiago
(74) *Attorney, Agent, or Firm* — RatnerPrestia

(57) ABSTRACT

A germicidal UV amalgam lamp with an elongated tubular lamp body and at least two filaments located on opposite ends of the lamp body. The lamp body is hermetically sealed with a pinch-sealed portion at both opposite ends, confining a gas volume in which a gas discharge can be produced along a discharge path between the filaments. Each filament has two electrical connectors, each including an internal portion connected to the filament and pinch-sealed into the lamp body. Each connector also includes an external portion located outside the lamp body for electrical connection of the lamp to a controlled power supply. The pinch-sealed portion bears a socket with an electrical temperature sensor and at least two electrical connections mounted to the
(Continued)

socket. The at least two electrical connections of the temperature sensor are connected in parallel to the electrical connectors of the filament.

21 Claims, 2 Drawing Sheets

(51) Int. Cl.
*C02F 1/32* (2006.01)
*H01J 7/44* (2006.01)
*H01J 61/52* (2006.01)
*H01J 61/72* (2006.01)

(52) U.S. Cl.
CPC ............ *H01J 61/523* (2013.01); *H01J 61/72* (2013.01); *A61L 2202/11* (2013.01); *C02F 2201/326* (2013.01)

(56) References Cited

U.S. PATENT DOCUMENTS

| | | | |
|---|---|---|---|
| 5,124,131 A | | 6/1992 | Wekhof |
| 5,237,240 A | * | 8/1993 | Bouchard ............... H01J 61/24 |
| | | | 313/15 |
| 5,271,305 A | | 12/1993 | Peters et al. |
| 5,274,305 A | * | 12/1993 | Bouchard ............... H01J 61/28 |
| | | | 315/108 |
| 7,420,183 B2 | | 9/2008 | Kaiser et al. |
| 8,018,130 B2 | | 9/2011 | Van der Broek et al. |
| 2006/0267495 A1 | * | 11/2006 | Pirovic ................... A61L 2/10 |
| | | | 313/547 |
| 2009/0065413 A1 | * | 3/2009 | Fraser ................... H01J 61/52 |
| | | | 210/175 |
| 2012/0112637 A1 | * | 5/2012 | Rooijackers ......... H05B 41/295 |
| | | | 315/117 |
| 2013/0229118 A1 | * | 9/2013 | Lucz .................... H05B 41/295 |
| | | | 315/182 |
| 2013/0309131 A1 | | 11/2013 | Engelhard |

FOREIGN PATENT DOCUMENTS

| | | | | |
|---|---|---|---|---|
| DE | 10129755 A1 | * | 1/2003 | ............ H05B 41/36 |
| DE | 10129755 A1 | | 1/2003 | |
| DE | 102006033672 A1 | | 1/2008 | |
| EP | 1484342 A1 | | 10/2004 | |
| EP | 2348797 A1 | | 7/2011 | |
| EP | 2451253 A2 | | 5/2012 | |
| FR | 2094720 A5 | | 2/1972 | |
| JP | 56120066 A | * | 9/1981 | ............ H01J 61/52 |
| JP | 11309451 A | | 11/1999 | |
| JP | 2003059307 A | * | 2/2003 | |
| JP | 2016184514 A | * | 10/2016 | |
| JP | 2016184514 A | | 10/2016 | |

OTHER PUBLICATIONS

International Preliminary Report on Patentability and Written Opinion for international Application No. PCT/EP2019/051791, dated Jul. 28, 2020, 8 pages.

* cited by examiner

GERMICIDAL AMALGAM LAMP WITH TEMPERATURE SENSOR FOR OPTIMIZED OPERATION

CROSS-REFERENCE TO RELATED APPLICATIONS

This patent application is a U.S. National Phase Patent Application of PCT Application No.: PCT/EP2019/051791, filed Jan. 24, 2019, which claims priority to European Patent Application No. 18153198.9, filed Jan. 24, 2019, each of which is incorporated by reference herein in its entirety.

The present invention relates to a germicidal UV amalgam lamp with the features of the pre-characterizing portion of claim 1 and to a method with the features of the pre-characterizing portion of claim 8.

Germicidal lamps, in contrast to lamp for lighting purposes, are optimized for their UV output especially in the wavelength range around 260 nm. Key features are total UV output at that wavelength and a good efficiency in terms of UV radiation power versus electric power consumption. In addition to that, germicidal lamps are commonly used in large scale installations for example for disinfecting waste water or drinking water. These installations make use of many lamps, sometimes of the order of hundreds. In this connection, not only operating efficiency, but also a long service life is important to the users of these installations, because both factors affect the overall operating costs. It may be a decisive factor in municipal installations, which compete with chlorination, ozonisation and reverse osmosis.

There are operating parameters that vary with temperature.

EP 2 348 797 A1 for example shows a lighting bulb of the compact fluorescent lamp type, which has a temperature sensor, integrated into the electronic driver of the gas discharge burner. Thus, separate wiring from an external sensor to the driver can be omitted. The teaching is that, if the temperature sensor at this position detects a high temperature, the driver might not restart the lamp immediately because a so-called "hot restart" would significantly shorten the service life of the lamp. These considerations are relevant for lighting equipment, which may frequently be switched on and off.

US 2013/0309131 A1 shows a germicidal lamp of the low pressure mercury amalgam type. These lamps, which are also the subject of the present invention, are sensitive to the temperature of the "cold spot", at which the amalgam is positioned. The mercury partial pressure inside the lamp, more correctly in the gas filling, depends on that temperature. In this document, the use of a temperature sensor close to the cold spot, and not inside the lamp, but between the lamp and a housing is suggested. The temperature measurement at this point enables the lamp current being controlled in order to achieve a desired operating temperature of the cold spot of the lamp and thus optimizing the operating point for efficiency.

To the same purpose, U.S. Pat. No. 8,018,130 B2 suggests to place a temperature sensor inside the gas volume of the lamp close to the amalgam. Hence, all documents deal with the temperatures under continuous operation of the germicidal lamp, mainly to avoid too high temperatures, which might damage the amalgam. In addition, all temperature sensors require separate, dedicated contact means which make the installation and operation more complicated, because care must be taken that not only the lamp contacts, but also the sensor contacts are properly mounted upon installation of the lamp.

These documents do not disclose a temperature sensor wired in parallel to one of the filaments, thus making use of the filament contacts, or an operating method for optimizing the process of starting a germicidal lamp from cold temperatures.

It is therefore an object of the present invention to suggest a germicidal lamp and a method of operating such a lamp which especially improve the start-up process from cold temperatures, because this process, if incorrectly handled, may lead to damage of the electrode filaments and thus also shorten the service life of the lamp.

This object is achieved by a germicidal lamp with the features of claim 1 and by a method according to claim 8.

In a germicidal UV amalgam lamp with an elongated tubular lamp body and at least two electrodes or filaments located on opposite ends of the lamp body, wherein the lamp body is hermetically sealed with a pinch-sealed portion at both opposite ends and confines a gas volume, in which a gas discharge can be produced along a discharge path between the filaments, and with two electrical connectors for each filament, the connectors having an internal portion being connected to one of the filaments and being pinch-sealed into the lamp body, and with an external portion which is located outside the lamp body for electrical connection of the lamp to a controlled power supply, in a way that the pinch-sealed portion carries a preferably ceramic socket part, an electrical temperature sensor with at least two electrical connections is mounted to the socket in the vicinity of the pinch-sealed portion of the lamp body. This allows a very good estimate of the filament or electrode temperature in the off-state of the lamp because, either the lamp has been switched off for a longer time, then both the filament and the sensor will be close to the ambient temperature, or they have been switched off recently, then they will both be at an elevated temperature. Anyway, without the gas discharge, the electrode and the temperature sensor will approximate an equilibrium on a short time scale of seconds or minutes because the gas discharge as a heat source has vanished. Thus, the measured temperature of the temperature sensor will be a good indicator of the lamp temperature and consequently allow the power supply to select the most appropriate starting parameters in terms of e.g. voltage and frequency. Furthermore, because the two electrical connectors of the temperature sensor are connected in parallel to the electrical connectors of the filament or in series with one electrical connector of the filament, the connectors of the filament can be used as connectors for the temperature sensor as well, reducing installation requirements. Different electrical operating schemes are possible.

Preferably the socket defines an internal void in which the sensor may be located. In a preferred embodiment, the sensor is sealed into the void in a watertight manner.

In addition to that, the position of the temperature sensor inside the socket body of the lamp is a very protected location with respect to mechanical or chemical stress or even too high temperatures. This makes the arrangement very rugged and reliable.

The device becomes even more robust if the connection of the temperature sensor to the filament is located inside the socket body.

When the temperature sensor is a metal wire sensor, especially a platinum wire sensor or a thermocouple, press-sealing these materials into a glass or even quartz enclosure will not lead to deterioration of the temperature sensing qualities.

The temperature measurement may be carried out or more easily or more precisely if the temperature sensor is a semiconductor sensor, especially a PTC or NTC sensor.

The temperature sensor may also be a bus controlled sensor and/or a microcontroller, which would be a preferred embodiment. In this case, information requests of a central common control unit can be directed to individual lamps. This would not only allow to gather information centrally, but also to compare temperature values of different lamps and thus do plausibility checks on the measured or transmitted temperature values.

In the method of operating a germicidal UV amalgam lamp, in which the temperature of an end portion of the lamp is determined using a temperature sensor being mounted close to one pinch-sealed end portion of the lamp, a very good estimate of the filament or electrode temperature in the off-state of the lamp is possible because, either the lamp has been switched off for a longer time, then both the filament and the sensor will be close to the ambient temperature, or they have been switched off recently, then they will both be at an elevated temperature. As explained above, without the gas discharge, the electrode and the temperature sensor will approximate an equilibrium on a short time scale of seconds or minutes because the gas discharge as a heat source has vanished. Thus, the measured temperature of the temperature sensor will be a good indicator of the lamp temperature and consequently allow the power supply to select the most appropriate starting parameters in terms of e.g. voltage and frequency.

Preferably the temperature is determined before starting the lamp, so that start-up conditions are known. It is furthermore preferred when the lamp starting voltage and/or the lamp starting frequency is selected dependent upon the temperature, because this can help to avoid filament damage or premature ageing. In order to improve this filament protection, it is even more preferred, when one or both filaments of the lamp are electrically pre-heated before starting the lamp, if the temperature is below a predetermined threshold temperature.

A lamp may also have a temperature outside a predefinable envelope. In this case it is of great advantage, if the temperature is outside a predetermined range or if no temperature can be measured at all, the lamp is not started.

The method may also comprise steps that are carried out during operation of the lamp in order to monitor operating points of the lamp. In case of over temperature or under temperature during operation of the lamp, the operation of the lamp is terminated if the temperature is past a first predetermined threshold value.

Further advantages can be achieved improving the safety of large installations, for example in municipal water or waste water works, in which the lamp is a member of a lamp group or array, the operation of the whole group or array is terminated if the temperature is above a predetermined threshold or if the temperatures of two lamps of the same group or array both exceed a predetermined threshold. Especially in the second case, the simultaneous overheating of two or more lamps can indicate a condition in which not the lamp itself causes thermal problems, but an external problem may be present. This could be the installation running dry for whatever reasons, or even a fire. A shutdown of the installation might in one of these cases avoid further damage.

The lamp controller may with benefit be used to estimate an amalgam temperature of the lamp on the basis of the temperature and optionally at least one additional parameter. In continuous operation, there may be a rather close relationship between the temperature at the position of the temperature sensor, i.e. close to the pinch-sealed end of the lamp, and the amalgam deposit which is some distance remote from that location. An equilibrium of that ratio can be expected some time after the start-up of the lamp. Then, the amalgam temperature can reliably be calculated from the temperature of the temperature sensor. In other cases, if no sufficient equilibrium state can be assumed, another parameter like lapsed running time, electric power input or ambient temperature might be taken into consideration. Having a good estimate of the amalgam temperature is helpful in choosing the operating point of the lamp with respect to efficiency and durability of the lamp.

To this end, the electrical power supplied to the lamp may be controlled in dependency of the temperature.

Two preferred embodiments of the invention will be described in the following with reference to the drawings, in which FIG. 1 shows one end portion of a germicidal UV lamp of the low pressure type with a temperature sensor in electrically parallel connection with the filament;

The lamp 2 comprises a lamp body 3, which is made of technical quartz glass, because this material allows ultraviolet radiation down to 200 nm to pass through the material without significant absorption. The lamp body 3 encloses a hermetically sealed gas volume 4, which usually is filled with a noble gas at low pressure. The length of the lamp body 3 and the gas volume 4 may be between 0.1 m and 2 m, preferably between 1 m and 2 m.

Figure 1:
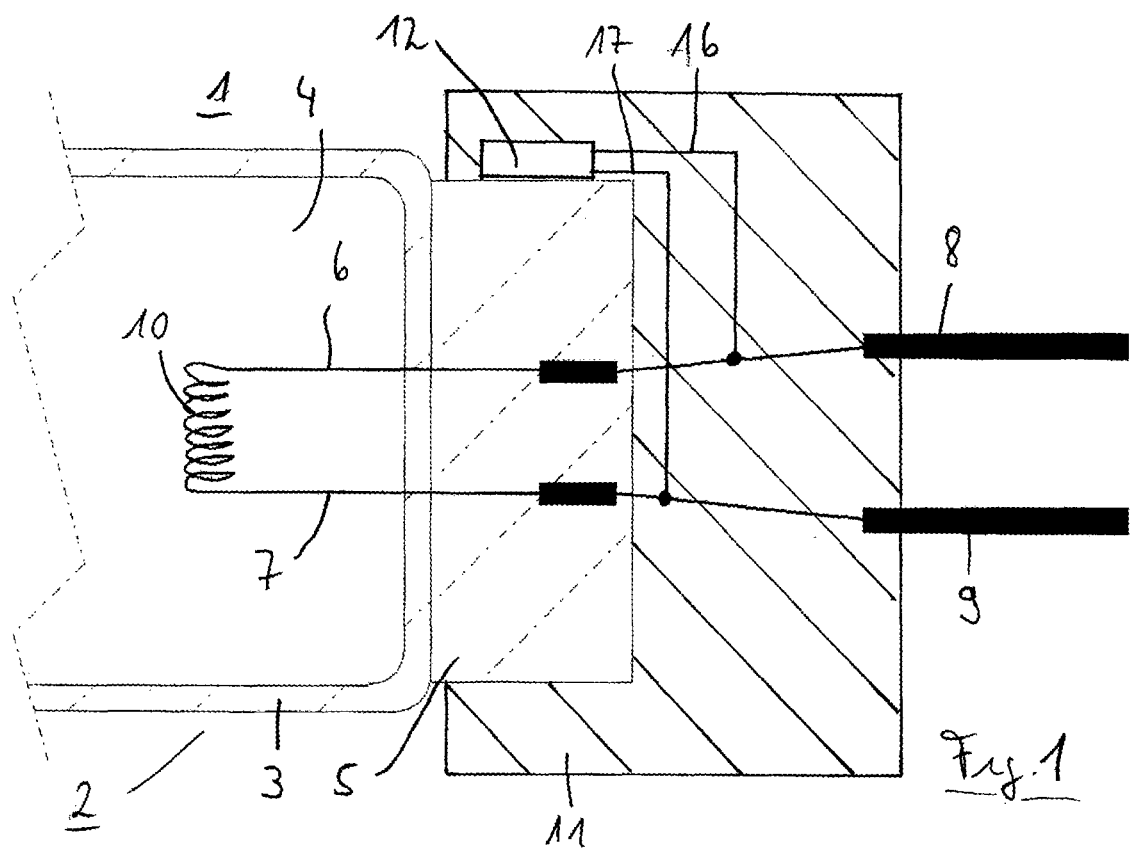
FIG. 1 shows one end portion 1 of a germicidal UV lamp 2. The lamp may be of the low-pressure mercury amalgam gas discharge type, which is widely in use in drinking water and wastewater disinfection installations.

The tubular lamp body 3 is hermetically sealed at both ends. The end 1 shown in FIG. 1 is sealed in a pinch-sealed portion 5, which essentially is a portion in which the lamp body 3 has been constricted and then pressed flat using an elevated temperature at which the material of lamp body 3 can be plastically deformed. The pinch-sealed portion 5 may be of the same material as the lamp body 3, so that a uniform tube of material can be used in the production process. The portion 5 can, however, also be made from another material like technical glass, which is fused to the lamp body 3 in order to allow plastic deformation at lower temperatures than would be necessary in the treatment of quartz glass.

Inside the pinch-sealed portion 5, there are electrical leads, namely a first electrically conducting wire 6 and a second electrically conducting wire 7. The wires 6 and 7 are sealed into the pinch-sealed portion 5 in a gas-tight manner. The wire 6 is connected to an external connecting pin 8, which is located outside the pinch-sealed portion 5 in order to be connected in a known manner, to a socket (not shown). Likewise, wire 7 is connected to a connecting pin 9, which is arranged in parallel to the pin 8.

The wire 6 leads to the inside of the lamp 2, namely into the gas volume 4 which is surrounded by the lamp body. It extends into the gas volume 4 and is electrically and mechanically connected to a filament 10. The filament 10, on the other hand, is also connected to wire 7 and is thus an element of an electric circuit going from pin 8 to pin 9 through the wires 6, 7 and the filament 10.

A socket 11, which may be made from ceramic material, encloses the pinch-sealed portion 5. The pins 8 and 9 are firmly held within the socket 11, and the electric connection between wires 6 and 7 and pins 8 and 9 is protected by the surrounding socket 11.

Furthermore, FIG. 1 shows a temperature sensor 12, which is located inside the socket 11 and is connected, via wires 16 and 17, to pins 8 and 9.

An electric current which is applied to the pins 8 and 9 will therefore flow from pin 8 through wire 6, filament 10 and wire 7 to pin 9. This is the supply current to drive the lamp 2 in a manner that is known in the art.

The position of the sensor 12 inside the socket 11 may be chosen according to requirements. In this preferred embodiment, the sensor 12 is located close to the pinch-sealed end 5.

The temperature sensor 12 is connected in parallel to the filament 10. The wires 16 and 17, which are connected to the sensor 12, are directly contacted with wires 6 and 7 respectively.

In this embodiment, due to the parallel connection between sensor 12 and filament 10, the temperature measurement and the electric power supply of the lamp operate through the same pins 8 and 9 of the lamp 2. Thus, the temperature measurement can be carried out by reading out the sensor 12 before applying the power to the filament 10, which means that the temperature can be measured directly before the startup of the lamp 2. The measurement can also be carried out during operation of the lamp 2, for example with a digital sensor 12, which can be read out using a digital signal which is modulated onto the drive current which is supplied to the filament 10.

Figure 2:
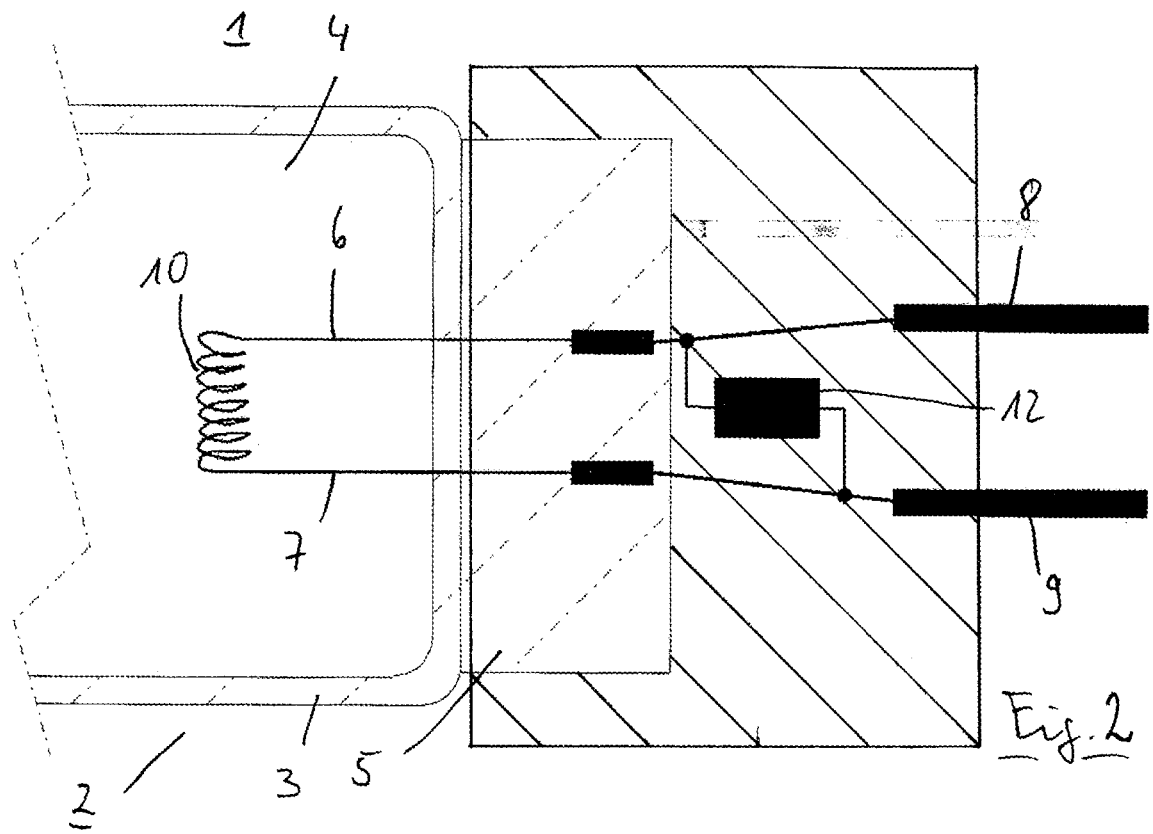
FIG. 2 shows an end portion of a germicidal UV lamp like in FIG. 1, but with a temperature sensor at another position in the socket.

FIG. 2 shows another end portion 1 of the lamp 2, in which the sensor 12 is wired parallel to the filament 10, like in FIG. 1. The location of sensor 12 is chosen such that the sensor is positioned almost centrally inside the ceramic socket 11.

Figure 3:
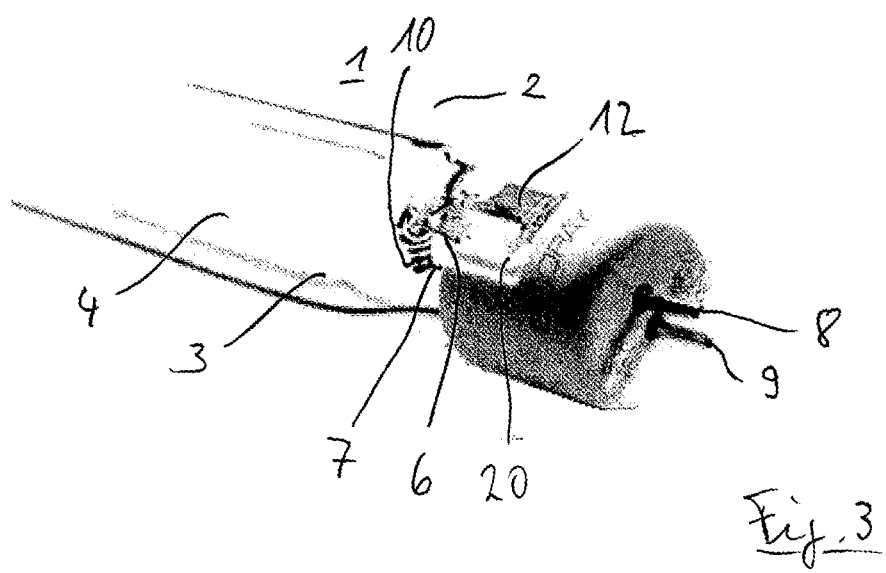
FIG. 3 shows the end portion of FIG. 2 in a more realistic perspective representation.

FIG. 3 finally shows a lamp 2 in a perspective view. The representation is more realistic than the schematic drawings of FIGS. 1-2. What is shown in FIG. 3 is the socket 12 at the end of lamp 2 with the pins 8, 9.

The sensor 12 is placed inside a cavity or void 20 which is provided in the socket 11. The sensor 12 is fixed inside the void 20 with a temperature resistant adhesive. If the sensor 12 needs to be protected from outside influences like water etc., the void 20 may be completely filled with resin or cement, so that the sensor 12 is completely sealed in the void 20.

The socket 11 with its connecting pieces 8, 9 can be taken as a mechanic and electric connecting element, which may be plugged into an appropriate socket for electrically contacting the lamp 2.

In operation, the temperature sensor 12 can electronically be checked to retrieve a temperature signal before starting the lamp 2. Depending on the result of this measurement, a control system (not shown) can select appropriate voltage and frequency for starting the electric discharge between filament 10 and a second filament (not shown) at the other end of the lamp 2. If the temperature is below a certain threshold value, the electronic control can choose to pre-heat the filament 10 by applying a DC voltage to the pins 8 and 9. Pre-heating the filament 10 will assist the formation of free electrons close to the surface of filament 10 and consequently lead to lower high-voltage being needed for starting the gas discharge.

In continuous operation, the temperature sensor 12 may from time to time or continuously be read out in order to gather information on the status of the lamp 2. After a certain time of operation, a steady state of temperature will be achieved, which is representative of the status of the lamp. An error condition might be detected, if the temperature of the sensor 12 is outside predetermined range, which range would be chosen on the basis of the present operating conditions. Such a temperature deviation might indicate an overload, dry-running or failure of the lamp, which would trigger a signal indication the necessity for service.

Finally, the use of the temperature sensor 12 could be extended to applications in which, before starting the lamp, the temperature values are checked for plausibility. If unexpected deviations between several lamps or a deviation of the temperature of one lamp from a default value are detected, the start-up of the lamp or the entire installation can be prohibited. Such a condition might indicate that the respective lamp 2 with is associated with an unexpected temperature signal is damaged or could otherwise lead to a malfunction. It can specially be avoided to send the high voltage ignition pulse to a lamp with such condition so that potential hazards resulting therefrom can be avoided. This adds to the safety in operation of the whole installation.

The invention claimed is:

1. A germicidal UV amalgam lamp comprising:
an elongated tubular lamp body hermetically sealed at opposite ends with pinch-sealed portions, the body confining a gas volume, each pinch-sealed portion bearing a socket;
at least two filaments located on the opposite ends of the lamp body within the gas volume and configured to produce a gas discharge along a discharge path between the filaments, each filament comprising two electrical connectors, each electrical connector including an internal portion connected to the filament and pinch-sealed into the lamp body, and an external portion located outside the lamp body and configured for electrical connection of the lamp to a controlled power supply; and
an electrical temperature sensor mounted to each socket and having at least two electrical connections connected in parallel to the two electrical connectors of one of the filaments.

2. The germicidal UV amalgam lamp of claim 1, wherein the socket comprises a void and the temperature sensor is located inside the void.

3. The germicidal UV amalgam lamp of claim 2, wherein the temperature sensor is sealed into the void in a watertight manner.

4. The germicidal UV amalgam lamp of claim 1, wherein the connection of the temperature sensor to the filament is located inside the socket.

5. The germicidal UV amalgam lamp of claim 1, wherein the temperature sensor is a metal wire sensor.

6. The germicidal UV amalgam lamp of claim 5, wherein the metal wire sensor is a platinum wire sensor or a thermocouple.

7. The germicidal UV amalgam lamp of claim 1, wherein the temperature sensor is a semiconductor sensor.

8. The germicidal UV amalgam lamp of claim 7, wherein the semiconductor sensor is a PTC or NTC sensor.

9. The germicidal UV amalgam lamp of claim 1, wherein the temperature sensor is a bus-controlled sensor or a microcontroller.

10. A method of operating a germicidal UV amalgam lamp, the lamp comprising a lamp body having at least one pinch-sealed end portion, a gas volume within the lamp body, a socket adjacent the at least one pinch-sealed end portion, and at least one filament disposed within the gas volume and having two electrical connectors for connection to a power supply, the method comprising:
- providing a temperature sensor integrated into a socket adjacent the pinch-sealed end portion of the lamp and having at least two electrical connections connection in parallel to the two electrical connectors of the filament; and
- using the temperature sensor to measure temperature of an end portion of the lamp.

11. The method of claim 10, comprising measuring the temperature with the temperature sensor before starting the lamp.

12. The method of claim 11, comprising selecting a lamp starting voltage or a lamp starting frequency dependent upon the temperature measured by the temperature sensor.

13. The method of claim 10, comprising electrically preheating a filament of the lamp before starting the lamp when the temperature measured by the temperature sensor is below a predetermined threshold value.

14. The method of claim 10, comprising not starting the lamp when the temperature measured by the temperature sensor is outside of a predetermined range or when the temperature sensor is unable to measure the temperature.

15. The method of claim 10, comprising controlling electric power supplied to the lamp dependent upon the temperature measured by the temperature sensor.

16. A method of operating a germicidal UV amalgam lamp, comprising:
- using a temperature sensor integrated into a socket adjacent a pinch-sealed end portion of the lamp to measure temperature of an end portion of the lamp, and
- terminating operation of the lamp if the temperature measured by temperature sensor is above a predetermined threshold value.

17. The method of claim 16, wherein the lamp is a member of a lamp group or array and the method comprises terminating operation of the lamp group or array as a whole when the temperature measured by temperature sensor is above the predetermined threshold value.

18. The method of claim 16, wherein the lamp is a member of a lamp group or array and the method comprises terminating operation of the lamp group or array as a whole when the temperatures measured by temperature sensors of two lamps of the lamp group or array both exceed the predetermined threshold value.

19. A method of operating a germicidal UV amalgam lamp, comprising:
- using a temperature sensor integrated into a socket adjacent a pinch-sealed end portion of the lamp to measure temperature of an end portion of the lamp, and
- using a lamp controller to estimate an amalgam temperature of the lamp based upon the temperature measured by temperature sensor.

20. The method of claim 19, further comprising basing the estimate of the amalgam temperature of the lamp on at least one other parameter in addition to the temperature measured by temperature sensor.

21. The method of claim 20, wherein the at least one other parameter comprises operating time of the lamp, electric power consumption of the lamp, or ambient temperature.

* * * * *